United States Patent [19]

Hoffman et al.

[11] Patent Number: 5,618,316

[45] Date of Patent: Apr. 8, 1997

[54] POLYETHYLENE OXIDE COATED INTRAOCULAR LENS

[76] Inventors: Allan S. Hoffman, 4528 W. Laurel Dr., N.E., Seattle, Wash. 98105; Anilbhai S. Patel, 4202 Brownwood La., Arlington, Tex. 76017; Gerard Llanos, 2625 Cockrell Ave., Fort Worth, Tex. 76109

[21] Appl. No.: 166,033

[22] Filed: Dec. 14, 1993

[51] Int. Cl.⁶ ..................................... A61F 2/14
[52] U.S. Cl. ............................... 623/6; 427/164
[58] Field of Search .................. 623/6; 427/2, 535, 427/536, 488; 523/106; 264/1.4, 1.7; 351/160 R, 160 H

[56] References Cited

U.S. PATENT DOCUMENTS

| 4,170,043 | 10/1979 | Knight et al. ............................ 623/6 |
| 4,280,970 | 7/1981 | Kesting ............................ 264/217 X |
| 4,312,575 | 1/1982 | Peyman et al. ............................ 264/1.7 |
| 4,656,083 | 4/1987 | Hoffman et al. ............................ 427/2 X |
| 4,731,080 | 3/1988 | Galin ............................ 623/6 |
| 4,740,533 | 4/1988 | Su et al. ............................ 523/106 |
| 4,834,750 | 5/1989 | Gupta ............................ 623/6 |
| 4,871,785 | 10/1989 | Froix ............................ 523/106 |
| 4,955,901 | 9/1990 | Nishiguchi et al. . |
| 5,002,794 | 3/1991 | Ratner et al. ............................ 427/535 X |
| 5,070,166 | 12/1991 | Su et al. ............................ 523/106 X |
| 5,080,924 | 1/1992 | Kamel et al. ............................ 623/6 X |
| 5,096,626 | 3/1992 | Tukamizawa et al. ............................ 264/1.7 |
| 5,116,361 | 5/1992 | Kim et al. . |
| 5,169,720 | 12/1992 | Braatz et al. . |
| 5,252,714 | 10/1993 | Harris et al. . |
| 5,275,838 | 1/1994 | Merrill ............................ 427/2 |
| 5,290,548 | 3/1994 | Goldberg et al. . |
| 5,290,892 | 3/1994 | Namdaran et al. ............................ 623/6 X |
| 5,308,641 | 5/1994 | Cahalan et al. ............................ 427/2 |
| 5,326,584 | 7/1994 | Kamel et al. ............................ 427/491 |
| 5,331,073 | 7/1994 | Weinschenk, III et al. ............................ 623/6 X |

FOREIGN PATENT DOCUMENTS

| 0415845 | 3/1991 | European Pat. Off. . |
| 6054900 | 1/1994 | Japan . |
| 93/00391 | 1/1993 | WIPO . |
| 94/16648 | 8/1994 | WIPO . |

*Primary Examiner*—David Isabella

[57] ABSTRACT

An intraocular lens having improved biocompatibility is coated with polyethylene oxide through covalent bonding, preferably using a plasma-deposited amine layer. The lens is then sterilized with ethylene oxide and extracted with water.

16 Claims, No Drawings

POLYETHYLENE OXIDE COATED INTRAOCULAR LENS

This invention was made with government support under Grant No. GM 4011 awarded by the National Institutes of Health. The United States Government has certain rights in the invention.

BACKGROUND OF THE INVENTION

This invention relates to intraocular lenses and more particularly, relates to intraocular lenses which have been coated with polyethylene oxide in a manner which improves biocompatibility.

BACKGROUND ART

Intraocular lenses (IOL) are well known in the field of ophthalmology. An intraocular lens, when surgically implanted in the eye, can be used to replace a natural lens which has been diseased by cataracts. Such lenses can also be placed in the eye to compensate for refractive errors. The optical portion of such lenses may be formed of various materials. One type of lens is the so-called hard lens made of a polymethylmethacrylate (PMMA). Hard plastic lenses have excellent optical characteristics and good machining and polishing qualities. A second class of lenses include the flexible silicone lenses, but which are susceptible to discoloration. A third category of lenses comprises the soft (non-silicone type) lenses which are generally called hydrogel lenses. Soft lenses are usually made from polyHEMA. A fourth category of lenses includes soft acrylate lenses.

The implantation of intraocular lenses is recognized as a substantial surgical advantage, particularly in the treatment of cataracts. However, some problems still exist in their use since implantation of an intraocular lens may cause damage to the corneal endothelium, inflammatory responses within the anterior or posterior segment of the eye, as well as other problems. When an intraocular lens is inserted into the eye, the mechanics of insertion may lead to adhesion to the lens of delicate intraocular tissues and damage to these structures ensues either immediately or over long periods. When in position, the lenses may cause adhesions and damage intraocular tissues which may require removal and replacement of the lens. The lenses may also adsorb protein and become "fouled."

It is recognized in the art that lenses may be coated with a coating material. Thus, U.S. Pat. No. 4,170,043 discloses intraocular lenses coated with a film that dissolves slowly in water. This helps prevent endothelial damage upon implantation of the IOL. The coating dissolves within about 24 hours after implantation.

U.S. Pat. No. 4,731,080 discloses a coated intraocular lens, wherein the lens is coated with a non-smudging, biologically compatible hydrophobic crosslinked vinyl containing silicone polymer coating material.

U.S. Pat. No. 5,080,924 discloses a method of modifying the surface of a substrate using radio frequency plasma-induced grafting. In this procedure, which may be used on an intraocular lens, a first biocompatible material, preferably having pendant carboxylic acid or amine groups, is covalently grafted to the surface of a substrate polymer core by radio frequency plasma induction. A second biocompatible material then may be grafted to the first biocompatible material using a cross-linking agent. This patent does not suggest that a polyethylene oxide coating could be applied in this way.

A series of patents disclose contact lenses which are coated by various materials including polyethylene oxide. Such patents include Nos. 4,280,970; 4,871,785; 4,740,533; 5,070,166; and 5,096,626. U.S. Pat. No. 4,280,970 discloses coating a contact lens by grafting polyoxyethylene thereto. However, contact lenses and intraocular lenses are different products each with its different problems, so solutions to problems of contact lenses cannot be extrapolated into solving problems with intraocular lenses.

A problem remains in the art to provide coated intraocular lenses which have improved biocompatibility. The present invention meets this need by providing polyethylene oxide coated intraocular lenses wherein the polyethylene oxide coating is applied through covalent bonding.

SUMMARY OF THE INVENTION

It is accordingly one object of the present invention to provide an intraocular lens having improved biocompatibility.

It is a still further object of the invention to provide an intraocular lens having improved biocompatibility which is achieved by applying a polyethylene oxide coating to the lens surface through covalent bonding.

An even further object of the invention is to provide an intraocular lens wherein the biocompatibility of the lens is improved by applying a polyethylene oxide coating to the lens through amine covalent bonding.

Other objects and advantages of the present invention will become apparent as the description thereof proceeds.

In satisfaction of the foregoing objects and advantages, the present invention provides an intraocular lens having improved biocompatibility, said lens being coated with a polyethylene oxide through amine covalent bonding. The polyethylene oxide is covalently bound at the lens surface by the process steps comprising:

1) creating an active surface on said lens by plasma deposition;
2) reacting the active lens surface with a polyethylene oxide through covalent bonding; and
3) stabilizing the resultant coating.

DESCRIPTION OF THE INVENTION

The present invention relates to coated intraocular lenses. The intraocular lenses may be formed from any of the well known hard lenses formed from polymers including those formed from polymethylmeth-acrylate (PMMA) or acrylic lenses. Such lenses are well known in the art. The invention includes coating of soft acrylate lenses, such as those disclosed in U.S. Pat. No. 5,290,892. In one embodiment, the lens is formed from a copolymer with an elongation of at least 150% wherein the copolymer is formed from two monomers, the first of which is 2-phenylethyl acrylate and the second of which is 2-phenylethyl methacrylate, and a copolymerizable cross-linking monomer having a plurality of polymerizable ethylenically unsaturated groups such as 1,4-butanediol diacrylate. The first monomer may be present at a concentration about 65 wt. % and the second monomer may be present at a concentration of about 30 wt. %. An ultraviolet absorbing material such as 2-(3'-methallyl'-2-hydroxy-5'-methyl-phenyl)benzotriazole may also be included. The invention is applicable to all lens styles. The disclosures of the prior patents discussed above are hereby incorporated into this disclosure with respect to the disclosure and discussion of various types of intraocular lenses to which this invention is applicable.

According to this invention, the biocompatibility of such lenses is substantially improved by coating the lenses with a polyethylene oxide coating. The expression "biocompatible" means that the resultant intraocular lens coated with a polyethylene oxide film is more biologically compatible with the eye than known lenses when inserted into the eye. In particular, the biocompatibility of the lens is improved by the discovery that intraocular lenses coated with polyethylene oxide according to this invention have improved resistance to protein adsorption. This results in a lens which is "non-fouling" and resistant to cell deposition and therefore, more biocompatible than known lenses.

The lenses are coated with a polyethylene oxide in a special manner as described herein to obtain covalent bonding to the lens surface through an active intermediate layer. It has been discovered that the use of covalent bonding through an intermediate layer makes the polyethylene oxide coating, more adherent to the lens surface, and provides for a uniform continuous coating which has improved resistance to protein adsorption and cell deposition.

According to this invention, the lens is first provided with an active coating or layer on the lens surface to create an active primary amine layer. A preferred procedure is to create an active layer on the lens by plasma deposition of a polymer coating containing a primary amine. However, equivalent active intermediate layers may be used.

The primary amine layer is preferably formed by contacting the lens with an allyl amine or a lower alkyl amine of the formula $RNH_2$, wherein R is an alkyl or allyl group of about 3–12 carbon atoms. Preferably the alkyl or allyl amine is one of intermediate chain-length wherein R is an alkyl group of 5–8 carbons, and most preferably, is n-heptyl amine.

The alkyl or allyl amine may be applied to the lens surface in any desired manner; however, it is preferred to create the active primary amine layer by plasma deposition of the alkyl or allyl amine on the lens surface. Plasma deposition in general is known in the art as shown for example in U.S. Pat. Nos. 4,312,575 and 4,656,083, the disclosures of which are incorporated by reference.

According to this invention, plasma deposition of the primary amine layer on the lens is generally carried out in two steps. First, the lens is placed in an electrical glow discharge apparatus, wherein a gaseous atmosphere is provided, (e.g., argon), and then the gaseous atmosphere is subjected to an electrical glow discharge to clean the surface. The gas is then removed. In the second step, plasma ignition is carried out in the presence of the vapor of the primary amine under conditions to cause the amine to deposit or form a plasma and form an ultrathin coating of about 5–300 angstroms on the surface of the lens.

After the surface of the lens is treated with the amine, the lens surface containing the amine layer is then reacted with a polyethylene oxide. The polyethylene oxide should have terminal groups or caps which are reactive with the amine coating. Aldehyde terminated polyethylene oxides are especially preferred. Through this reaction of the polyethylene oxide and the amine attached to the lens surface in the presence of a reducing agent, a stable polyethylene oxide coating will be attached to the lens surface through the resultant covalent bonding. Such polyethyiene oxides are known in the art, e.g. from the publication by Harris, "Polymer Preprints", 32, 154 (1991).

The alkyl or allyl amine is applied by plasma deposition as indicated above. In a preferred procedure, the intraocular lens is first etched prior to amine deposition for best results. Preferably, etching of the surface is conducted by contact with argon. An argon flow rate in the range of 60–120 $cm^3$/min, and a chamber pressure of 200–300 mTorr is satisfactory. In conducting the deposition, the intraocular lens is placed in a holder and centered in a plasma chamber with the desired argon flow rate to argon etch prior to amine deposition. A container for the amine is connected to the plasma chamber unit. The plasma chamber is then evacuated to its baseline pressure and, while under the argon flow rate, is ignited for a short period, for example, 60 W for six minutes. After the argon etch, the plasma chamber is evacuated to its baseline pressure, the amine vapor is evacuated into the chamber, the plasma ignited, and the deposition permitted to be maintained until a thickness in the range of 5–500, preferably 100–300 Angstroms, is achieved. After the plasma is extinguished, the chamber conditions are maintained for a short period, for example, 1–5 minutes. The chamber is then brought to atmospheric conditions and the sample removed to a container such as a sealed microcentrifuge tube.

A polyethylene oxide (PEO), e.g., aldehyde capped polyethylene oxide, is dissolved in a buffer solution in a concentration in the range of 5–50 mg/ml and is preferably purified to remove any particulates. This solution is then added to each microcentrifuge tube containing the amine-plasma coated intraocular lens. Stabilization of the coating on the lens is then carried out by treating the lens with an alkali metal borohydride dissolved in a buffer in a concentration of 10–50 mg/ml. Reduction of the PEO amine bond with the alkali metal borohydride will provide a stable PEO coating of about 5–500 Angstroms, preferably 100–300 Angstroms. Mixing of the solution is preferably done by inverting the tubes.

The resulting samples are then heated at a low temperature, for example, 25°–50° C. for about ten to thirty hours. In a preferred procedure, stabilization is repeated and the lenses are again heated. Each lens is then washed in deionized water and the water removed.

A preferred polyethylene oxide utilized in the present invention is an aldehyde-terminated polyethylene oxide which has a molecular weight in the range of 200 to 100,000, preferably 1500–10,000. Such aldehyde-capped polyethylene oxides are known in the art, e.g., Harris, "Polymer Preprints", 32, 154 (1991). However, any polyethylene oxide having reactive terminal groups may also be used in the invention.

The preferred stabilizing agent is an alkali metal borohydride, most preferably sodium or potassium cyanoborohydride of the formula $NaCNBH_3$, a commercially available material.

An important aspect of the invention concerns sterilization of the coated lenses after preparation. The lenses may be sterilized using standard ethylene oxide sterilization and aeration to remove residual ethylene oxide. Sterilization with ethylene oxide comprises contact with 10–20% ethylene oxide in a fluoride solvent for 1–4 hours at 10–40 psi and 40°–60° C., preferably after preconditioning in a humid atmosphere. However, according to this invention, it has been discovered that aqueous extraction rather than aeration of the residual ethylene oxide following sterilization minimizes loss of protein and cell repulsion ability of the polyethylene oxide coating. Aqueous extraction comprises contact of the lens with 1–3 ml of sterile water per lens while heating at a temperature of about 25°–60° C. for 3–9 days. Theoretically, it appears the aqueous extraction prevents the polyethylene oxide chain from inverting. Also, since the water contains less oxygen than air, cleavage of the polyethylene oxide molecules may be reduced. It has been found that aqueous extraction efficiency also increases with temperatures ranges from 35° to 60° C. and time from 3 to 14 days. Residual ethylene oxide levels as low 6 ppm can be achieved. Further, the residual levels of epichlorohydrin and ethylene glycol which are byproducts of ethylene oxide extracted with water, are very low, i.e. less than 10 ppm and 50 ppm respectively. This is below industry standards so that extraction vials with water or buffers, for example, BSS, may also be used for final packaging.

The resulting intraocular lens will have the indicated improved biocompatibility including increased resistance to protein adsorption which makes the lens non-fouling and resistant to cell deposition.

The following examples are presented to illustrate the invention but the invention is not to be limited thereto. Parts are by weight unless otherwise indicated.

EXAMPLE 1

A. Surface Amination

PMMA IOLs (6 mm, plano-convex, single piece or monoflex-PMMA or polypropylene haptics) are each placed in a butterfly lens holder and the lens holder then positioned in a cleaned glass-rack. The glass rack is placed onto a larger glass rack centered in the plasma chamber.

n-Heptylamine (5.0 g) is placed in a 250 mL round bottom flask. The flask is connected via a rubber stopper to a metering-valve located at the front of the plasma chamber unit. With the needle valve to the heptylamine flask closed, the plasma chamber is evacuated to its baseline pressure of approximately 13 mTorr. This condition is maintained for thirty minutes.

The IOLs are argon-etched prior to n-heptylamine deposition. At an argon flow rate of 90 cm$^3$/min and a chamber pressure of 250 mTorr, a plasma is ignited at 60 W for six minutes. After the argon etch, the plasma chamber is evacuated to its baseline pressure.

n-Heptylamine vapor is introduced into the chamber of the plasma unit. Vacuum pump speed is lowered and the chamber is allowed to equilibrate for ten minutes. The plasma is ignited and a thickness monitor is activated to record deposition. The plasma is maintained until a thickness monitor reading of 190 Angstroms is achieved. After the plasma is extinguished, the chamber conditions are maintained for two minutes. Following this, the vacuum pump speed is returned to maximum and maintained for ten minutes. The chamber is brought up to atmospheric conditions by back-filling with argon. The samples are removed from their respective holders and each placed in a microcentrifuge tube containing PEO solution. B. PEO Immobilization

| Phosphate/Sulphate buffer: | 7.838 grams Potassium Sulphate ($K_2SO_4$) 0.060 grams Sodium phosphate dibasic ($Na_2HPO_4$) Deionized Water to final volume of 100 mL. |
|---|---|

Heating is required to dissolve the $K_2SO_4$. Final pH range 8.5–9.0.

Methoxy end-capped, dithiolaldehyde derivatized PEO of molecular weight 5000 (designated MPEG5KS2CHO), which can be made according to the procedure set forth in Harris et al., "Polymer Preprints", 32, 154 (1991), is dissolved in buffer at a concentration of 10 mg/mL. The solution is filtered through a fritted glass filter (coarse) to remove any particulates. MPEG5KS2CHO solution (900 μL) is added to each microcentrifuge tube containing plasma-coated IOL. Sodium cyanoborohydride ($NaCNBH_3$) is dissolved in the buffer at a concentration of 20 mg/mL. 100 μL of this solution is added to each microcentrifuge tube containing plasma-coated IOL. Each solution is gently mixed by inverting the tubes ten times. The $NaCNBH_3$ solution is hydrolytically unstable and should be prepared just prior to its addition to the reaction solution.

The samples are then heated at 35° C. overnight (16–18 hours). The treatment with $NaCNBH_3$ is repeated, and the samples heated at 35° C. for another four hours. Each IOL sample is washed by consecutive dip-rinsing in three beakers containing 140 mL of deionized water. Each IOL is then placed in 3 mL deionized water and sonicated for five minutes. This wash water is then replaced by fresh deionized water and sonication repeated. This last sonication step is repeated. (Three sonications in total). Each IOL is removed from wash solution, the excess water removed from the sample IOL, and then repackaged.

EXAMPLE 2

Biointeraction Studies

A. Protein Adsorption

As fibrinogen plays a significant role in the biocompatibility of implanted devices including intraocular lenses, its adsorption from single protein and multi-protein solutions was investigated. Human fibrinogen radiolabelled with $^{125}$Iodine was used to determine the amounts of adsorbed protein on the IOL surface. Prior to exposure to protein solutions the IOL samples (without haptics) were incubated at 37° C., for one hour in BSS (Balanced Salt Solution). In the single protein experiment each IOL was incubated at 37° C. for one hour in a BSS solution containing 5 μg/mL of $^{125}$I-fibrinogen. For the multi-protein experiment IOLs were exposed to 1:5:16 mixtures of $^{125}$I-fibrinogen, IgG and albumin at 37° C. for one hour. Fibrinogen concentrations at 125 μg/mL (Multi-protein A) and 62.5 μg/mL (Multi-protein B) were investigated. These protein concentrations were chosen to simulate post-operative human aqueous humor levels.

The protein adsorption results are reported as fractions of the amount adsorbed on uncoated PMMA IOL controls; and are summarized in Table 1. The results of the single protein study indicated that the heptylamine-plasma pre-coat marginally increased the amount of adsorbed fibrinogen over uncoated PMMA controls while the PEO coating reduced it by about 85%; PMMA adsorbed 158±30 ng/cm$^2$ fibrinogen. Similar levels of reduction were observed when PEO coated IOLs were exposed to higher protein concentrations in the simulated post-operative aqueous humor. The presence of albumin and IgG appeared not to significantly affect the amount of adsorbed fibrinogen.

TABLE 1

| | Fibrinogen Adsorption | | |
|---|---|---|---|
| Coating Type | Single protein (normalized)* | Multi-protein A† (normalized) | Multi-protein B‡ (normalized) |
| Heptyl-amine- | 1.10 ± 0.09 (n = 23) | 1.53 ± 0.37 (n = 2) | — |

TABLE 1-continued

| | Fibrinogen Adsorption | | |
|---|---|---|---|
| Coating Type | Single protein (normalized)* | Multi-protein A† (normalized) | Multi-protein B‡ (normalized) |
| plasma PEO | 0.13 ± 0.09 (n = 25) | 0.1 ± 0.06 (n = 11) | 0.10 ± 0.05 (n = 6) |

*Amount adsorbed normalized against that of PMMA controls.
† Fibrinogen (125 μg/mL), IgG (625 μg/mL) and Albumin (2 mg/mL)
‡ Fibrinogen (62.5 μg/mL), IgG (312.5 μg/mL) and Albumin (1 mg/mL)

B. Immunogold Staining

To visualize the pattern of adsorbed fibrinogen on IOL surfaces and to draw some inferences about the uniformity of PEO coating, a method involving antibodies linked with gold was utilized. IOL surfaces were first exposed to solutions of fibrinogen (single protein adsorption) and then incubated in the presence of rabbit anti-human fibrinogen antibody. The samples were subsequently reacted with goat anti-rabbit IgG-gold complex, amplified with silver particles and observed under a light microscope (100–400 ×magnifications). A uniform coating of gold-silver was observed on both PMMA and heptylamine-plasma coated surfaces while PEO surfaces appeared to be free of gold indicating little or no adsorbed protein.

C. Cell interactions (i) Human Macrophage Activation: Surface induced release of hydrogen peroxide from human macrophages was used to model the inflammatory response to PEO coated IOLs. As adsorbed protein can influence the extent of activation, the samples were pre-exposed to simulated post-surgical aqueous humor solution under experimental conditions similar to those described for the multi-protein adsorption study. The following methods describe how cultured human macrophages were seeded onto the IOL optic surface in serum-free culture medium for 2 hours at 37° C., followed by incubation in a phenol red-horseradish peroxidase solution for 1 hour at 37° C. After removing and making this solution alkaline, the peroxide concentration was determined at 630 nm. The results were reported as normalized values (against PMMA) and summarized in Table 2. The results indicated that the PEO coating significantly reduced acute macrophage activation on PMMA IOLs.

TABLE 2

| Human Macrophage Interactions. | |
|---|---|
| Surface | H$_2$O$_2$ Production (normalized) |
| PMMA | 1.00 ± 0.19 (n = 5) |
| PEO | 0.20 ± 0.10 (n = 7) |

(ii) Rabbit Lens Epithelial Cell Interaction: Along with repelling proteins from the surface of an implant, another function of immobilized PEO is to prevent the attachment and growth of cells (macrophages, neutrophils, epithelial cells, fibroblasts, etc.) which can ultimately lead to device failure. To quantify the potential of adhesion and growth of cells on the PEO coating an assay involving the incorporation of $^3$H-thymidine into the DNA of mitotic rabbit lens epithelial cells (LEC) was utilized. It should be noted that this assay was not intended as a method for assessing the ability of the PEO coating to prevent posterior capsule opacification. Briefly, the assay involved seeding cultured LEC onto the optic surface of both coated and uncoated IOLs in culture medium containing 5% serum and $^3$H-thymidine, followed by incubation for 2 days at 37° C. The cells were then fixed in 2% glutaraldehyde and their levels of radioactivity determined.

To investigate the role of protein adsorption on the growth of LEC, the assay was performed on bare surfaces as well as those pre-exposed to simulated post-surgical aqueous humor. As shown in Table 3, the PEO coating was unable to support the adhesion and growth of LEC irrespective of whether proteins were pre-adsorbed to the surface. Examination of the surfaces by phase-contrast light microscopy revealed only a few round cells on the PEO surface, while a fully confluent layer of spread cells was observed on PMMA and tissue-culture polystyrene controls. Rounded cells result from their inability to attach and spread on substrate surface. In the confluent layer the cells attained their natural polygonal morphology. It was interesting to note that pre-adsorption of protein to PMMA resulted in significantly more cell growth on the surface.

TABLE 3

| Rabbit Lens Epithelial Cell Interactions | |
|---|---|
| Surface | Normalized cell growth |
| PMMA | 1.00 ± 0.032 (n = 5)** |
| PEO* | 0.010 ± 0.005 (n = 5) |
| PEO | 0.021 ± 0.028 (n = 5) |

*pre-exposed to simulated post-surgical aqueous humor
**n is number test samples.

EXAMPLE 3

Sterilization Studies

The polyethylene oxide coated IOLs were sterilized with 12% ethylene oxide (in Freon) for two hours at 22–24 psi and 46° C., after a one hour preconditioning in a 60% relative humidity atmosphere. Each sterilized lens was then transferred to 3 mls of sterile water and heated at 60° C. for 7 days. The lenses were then stored (at RT) in this solution until used.

Results of a fibrinogen adsorption assay, shown in table, indicated that aqueous extraction restores the efficacy of the coating.

TABLE

| Normalized‡ Fibrinogen Adsorption | | |
|---|---|---|
| EO Sterilized Only | EO Sterilized and Aerated* | EO Sterilized & Aqueous Extracted |
| 0.35 ± 0.20 n = 9 | 0.6 ± 0.14 n = 8 | 0.18 ± 0.09 n = 5 |

‡ Amount of fibrinogen adsorbed on each lens was normalized against that on PMMA control.
*Following sterilization aerate for 8.5 days at 49° C. ± 2° C. under atmospheric pressure.

The invention has been described herein with reference to certain preferred embodiments; however, as obvious variations thereon will become apparent to those skilled in the art, the invention is not to be considered as limited thereto.

What is claimed is:

1. An intraocular lens having improved biocompatibility, said lens being a soft acrylate lens coated with an aldehyde terminated polyethylene oxide through amine covalent bonding, wherein an amine coating is formed from plasma deposition of a normal alkyl amine or allyl amine having about 3–12 carbon atoms, and the polyethylene oxide coating attaches to the lens surface by reaction of terminal aldehyde groups with active primary amine groups in the plasma deposited coating.

2. An intraocular lens according to claim 1 wherein the amine is n-heptyl amine.

3. An intraocular lens according to claim 1 wherein the acrylate comprises a copolymer with an elongation of at least 150% wherein said copolymer is comprised of two monomers, the first of which is 2-phenylethyl acrylate and the second of which is 2-phenylethyl methacrylate, and a copolymerizable cross-linking monomer having a plurality of polymerizable ethylenically unsaturated groups.

4. An intraocular lens according to claim 1 wherein the acrylate comprises a copolymer with an elongation of at least 150% comprised of two monomers, the first of which is 2-phenylethyl acrylate, the second of which is 2-phenylethyl methacrylate, and a cross-linking monomer 1,4-butanediol diacrylate.

5. The intraocular lens of claim 3 wherein the first monomer is present at a concentration about 65 wt. % and the second monomer is present at a concentration of about 30 wt. %.

6. The intraocular lens of claim 3 wherein said cross-linking monomer is 1,4-butanediol diacrylate.

7. The intraocular lens of claim 1 further comprising an ultraviolet absorbing material.

8. The intraocular lens of claim 7 wherein the ultraviolet absorbing material is 2-(3'-methallyl'-2-hydroxy-5'-methylphenyl) benzotriazole.

9. An intraocular lens having improved biocompatibility and improved resistance to protein absorption and cell deposition, said lens being a PMMA lens having a first layer thereon, said layer comprising an amine coating formed on the surface of the lens by plasma deposition of a member selected from the group consisting of a normal alkyl amine and an allyl amine, each of said amines having about 3–12 carbon atoms, said amine layer being a functional amine layer deposited from a plasma to form an ultrathin layer of about 5–300 Angstroms on the surface of said lens; and further comprising a second layer of a polyethylene oxide coating on the surface of said amine layer, said polyethylene oxide coating being formed by reaction of terminal aldehyde groups on said polyethylene oxide with the functional amine coating contained on the lens surface, said reaction of aldehyde groups and functional amine being carried out in the presence of a reducing agent so that a stable polyethylene oxide coating is attached to the amine layer contained on the lens surface through covalent bonding, said stable polyethylene oxide layer having a thickness of about 5–500 Angstroms, and wherein said polyethylene oxide is an aldehyde terminated polyethylene oxide having a molecular weight in the range of 200–100,000.

10. An intraocular lens according to claim 9, wherein after formation of said polyethylene oxide layer thereon, said coated lens is sterilized with ethylene oxide and then extracted with water at 25°–60° C. for 3–9 days to remove residual ethylene oxide and to minimize loss of protein and cell repulsionability of the polyethylene oxide layer.

11. An intraocular lens having improved biocompatibility and improved resistance to protein absorption and cell deposition, said lens having a first layer thereon, said layer comprising an amine coating formed on the surface of the lens by plasma deposition of a member selected from the group consisting of a normal alkyl amine and an allyl amine, each of said amines having about 3–12 carbon atoms, said amine layer being a functional amine layer deposited from a plasma to form an ultrathin layer of about 5–300 Angstroms on the surface of said lens; and further comprising a second layer of a polyethylene oxide coating on the surface of said amine layer, said polyethylene oxide coating being formed by reaction of terminal aldehyde groups on said polyethylene oxide with the functional amine coating contained on the lens surface, said reaction of aldehyde groups and functional amine being carried out in the presence of a reducing agent so that a stable polyethylene oxide coating is attached to the amine layer contained on the lens surface through covalent bonding, said stable polyethylene oxide layer having a thickness of about 5–500 Angstroms, and wherein said polyethylene oxide is an aldehyde terminated polyethylene oxide having a molecular weight in the range of 200–100,000.

12. An intraocular lens according to claim 11, wherein after formation of said polyethylene oxide layer thereon, said coated lens is sterilized with ethylene oxide and then extracted with water at 25°–60° C. for 3–9 days to remove residual ethylene oxide and to minimize loss of protein and cell repulsionability of the polyethylene oxide layer.

13. An intraocular lens according to claim 11, wherein the amine is n-heptyl amine.

14. An intraocular lens according to claim 11 wherein the lens is a soft acrylate lens.

15. An intraocular lens according to claim 9 wherein the amine is n-heptyl amine.

16. An intraocular lens according to claim 9 wherein the polyethylene oxide coating is about 100–300 Angstroms in thickness.

* * * * *